United States Patent
Mcclymont et al.

(10) Patent No.: US 11,529,133 B2
(45) Date of Patent: Dec. 20, 2022

(54) SURGICAL ACCESS INSTRUMENT

(71) Applicant: K2M, Inc., Leesburg, VA (US)

(72) Inventors: Kaitlin Elizabeth Anne Mcclymont, Reston, VA (US); Erica Lynn Marron, Leesburg, VA (US); Kern Singh, Chicago, IL (US); Sheeraz Qureshi, New York, NY (US); Mark Kurd, Wayne, PA (US); Callie Frances Turlington, Falls Church, VA (US)

(73) Assignee: K2M, Inc., Leesburg, VA (US)

( * ) Notice: Subject to any disclaimer, the term of this patent is extended or adjusted under 35 U.S.C. 154(b) by 0 days.

(21) Appl. No.: 17/017,950

(22) Filed: Sep. 11, 2020

(65) Prior Publication Data
US 2021/0068802 A1 Mar. 11, 2021

Related U.S. Application Data

(60) Provisional application No. 62/898,804, filed on Sep. 11, 2019.

(51) Int. Cl.
*A61B 17/02* (2006.01)

(52) U.S. Cl.
CPC ...... *A61B 17/0218* (2013.01); *A61B 17/0293* (2013.01)

(58) Field of Classification Search
CPC ............ A61B 17/0218; A61B 17/0293; A61B 17/0256; A61B 17/3421; A61B 17/3423; A61B 17/3445; A61B 2017/0256; A61B 2017/3445

USPC ......................................................... 600/235
See application file for complete search history.

(56) References Cited

U.S. PATENT DOCUMENTS

| | | | |
|---|---|---|---|
| 4,181,123 A | 1/1980 | Crosby | |
| 5,785,648 A | 7/1998 | Min | |
| 6,616,603 B1 | 9/2003 | Fontana | |
| 7,824,410 B2 | 11/2010 | Simonson et al. | |
| 8,052,720 B2 | 11/2011 | Kuester et al. | |
| 8,444,678 B2 | 5/2013 | Simonson et al. | |
| 9,226,782 B2 | 1/2016 | Simonson et al. | |
| 9,968,348 B2 * | 5/2018 | Vennard | A61B 17/0218 |
| 10,524,831 B2 | 1/2020 | Mather et al. | |
| 2005/0277811 A1 | 12/2005 | Richards et al. | |
| 2006/0106416 A1 * | 5/2006 | Raymond | A61B 17/02 606/198 |
| 2006/0287583 A1 * | 12/2006 | Mangiardi | A61B 1/32 600/210 |
| 2011/0022165 A1 | 1/2011 | Oba et al. | |
| 2011/0040333 A1 * | 2/2011 | Simonson | A61M 29/02 606/279 |
| 2012/0095297 A1 * | 4/2012 | Dang | A61B 17/3439 600/208 |

(Continued)

*Primary Examiner* — Eduardo C Robert
*Assistant Examiner* — Christina Negrellirodriguez
(74) *Attorney, Agent, or Firm* — Lerner, David, Littenberg, Krumholz & Mentlik, LLP

(57) ABSTRACT

In one embodiment, an access instrument for creating a surgical working portal includes a body having a first end and a body length, a first slot having a first slot length running along the length of the body from the first end, and a second slot having a second slot length running along the length of the body from the first end, wherein the first slot length and the second slot length are less than the body length.

20 Claims, 13 Drawing Sheets

(56) References Cited

U.S. PATENT DOCUMENTS

2014/0121467 A1* 5/2014 Vayser ................ A61B 17/025
600/214
2016/0270816 A1* 9/2016 Mather .................... A61B 1/07

* cited by examiner

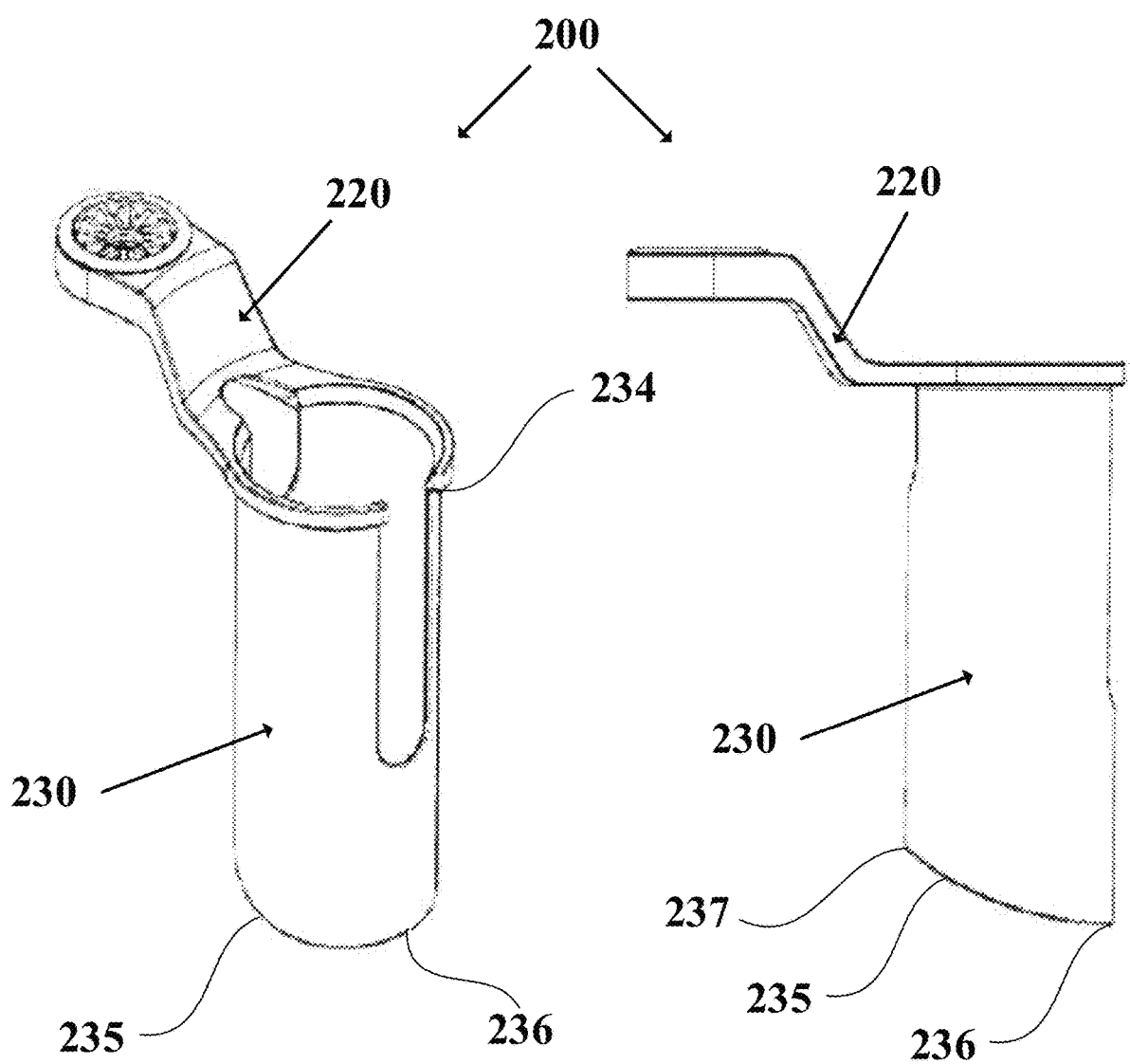

SURGICAL ACCESS INSTRUMENT

CROSS-REFERENCE TO RELATED APPLICATIONS

The present application claims the benefit of the filing date of U.S. Provisional Patent Application Ser. No. 62/898,804, filed on Sep. 11, 2019, the disclosure of which is hereby incorporated herein by reference.

BACKGROUND OF THE INVENTION

Different surgical procedures utilize different surgical access devices depending upon the type of surgery being performed and the approach desired by the surgeon. For instance, spinal surgeries may be performed as open or minimally invasive surgeries. In the former, large scale incisions are utilized to open a patient's body to directly expose the spine. This type of surgery may be desired due to a variety of considerations, including the complexity of the procedure and level of access to the spine that is required. On the other hand, minimally invasive surgery ("MIS") in the spine generally involves making smaller incision(s) and conducting most of the surgery within the patient itself. This often results in less trauma to the soft tissue of the patient as compared to an open surgery, which can result in quicker healing, less scarring, and less risk of intra- and post-operative complications.

Although MIS has many benefits, it often requires a different set of instruments than those used in an open surgery. For instance, in a spinal MIS, a surgical access instrument (e.g., cannula or retractor) is typically inserted within the smaller incision to provide a working portal for the surgery. This access instrument holds back a patient's tissue so that visualization can be maintained and tools can be inserted into the working portal without the fear of damage to surrounding tissue from those inserted tools (e.g., tools that have sharp or abrasive edges). However, due to the restricted size of the incision (which can be as small as 2 cm), the size of the working portal is minimized; thus, limiting the visibility and range of movement of those tools.

Current solutions to this problem can lead to an increased risk of complexity in the surgery and trauma to the patient. For instance, one solution would be to constantly loosen the mounting arm and access instrument so that the access instrument can be readjusted according to the surgeon's needs at any given time. However, such readjustments are time consuming and can lead to tissue creeping within the working portal during each readjustment. Alternative solutions may involve the use of a larger access instrument. However, as the size of the access instrument increases, the size of the working portal increases; thereby increasing trauma to the patient and potentially requiring larger and larger incisions. Oval-shaped access instruments can partially increase the angular access and visibility to a working portal but is still restricted to a certain size and shape; thus, providing similar access to a non-oval-shaped access instrument but with greater tissue disruption. Full-length slot access instruments do not solve the problem of contra-lateral angular access and visibility, and runs the risk of decreasing structural strength and increasing tissue creep. Alternative access instruments such as split-tube and mini-open retractors also suffer defects in time consumption, as well as increasing the complexity of the surgery and increasing the size of the incision to the patient.

This present application includes an improved surgical access instrument that can provide a working portal for surgical tools to be inserted within a patient's body while also increasing the mobility and visibility of those tools within the patient.

BRIEF SUMMARY OF THE INVENTION

The present disclosure is directed to an access instrument, and methods of using the same. The access instrument has at least one slot running along a length of the body and a corresponding opening aligned with the at least one slot to serve as relief areas for a portion of an instrument inserted within the access instrument. In this manner the access instrument permits more angular freedom and greater visibility in the working portal of a patient during minimally invasive surgeries. Methods of using same are also disclosed and include using such access instrument in a spinal MIS.

In one embodiment, an access instrument for creating a surgical working portal includes a body having a first end and a body length, a first slot having a first slot length running along the length of the body from the first end, and a second slot having a second slot length running along the length of the body from the first end, wherein the first slot length and the second slot length are less than the body length. Further, the access instrument may include an extension having an engagement portion, a rim attached to the first end of the body, and an intermediate portion between the engagement portion and the rim. Further, the intermediate portion may extend from a transition portion of the rim, the transition portion defined between the intermediate portion and the rim. Further, the rim may define a first opening along a portion thereof and the transition portion defines a second opening along a central region of the transition portion. Further, the first slot of the body may be aligned with the first opening and the second slot is aligned with the second opening. Further, the first opening and the second opening may be circumferentially opposite each other. Further, a first angle may be formed between the intermediate portion and the engagement portion, and a second angle is formed between the intermediate portion and the rim, and the intermediate portion extends a proximal distance from the rim. Further, the engagement portion may include a securement portion selected from a hirth joint or a threaded joint. Further, either of the first slot length and the second slot length may be greater than the other. Further, the first slot length and the second slot length may be equal. Further, the rim may define a first circumferential plane and the body having a second end longitudinally opposite the first end defining a second circumferential plane, the first circumferential plane being either parallel or at a planar angle from the second circumferential plane. Further, the first slot may have a first width and the second slot has a second width, either of the first slot and the second slot being greater than the other. Further, the first opening may have a first distance and the second opening has a second distance, either of the first distance and the second distance being greater than the other.

In another embodiment, a method of using an access instrument includes inserting a first instrument within a passageway running through the port, and a body having a body length and a first end, inserting a second instrument within the passageway, maneuvering the first instrument through a first slot having a first slot length running along the length of the body from the first end, and maneuvering the second instrument through a second slot having a second slot length running along the length of the body from the first end, wherein each of the first slot length and the second slot length is less than the body length. Further, the method may further comprise mounting the access instrument by connecting an extension of the access instrument to a mounting arm. Further, the method may include securing a securement portion to the mounting arm. Further, the body may define a longitudinal axis, and maneuvering the first instrument may form a first angle between the first instrument and the longitudinal axis, and maneuvering the second instrument forms a second angle between the second instrument and the longitudinal axis, the first angle being greater than the second angle. Further, the extension may include a rim defining a first opening and a second opening circumferentially opposite each other, and maneuvering the first instrument includes maneuvering the first instrument through the first opening and maneuvering the second instrument includes maneuvering the second instrument through the second opening.

In another embodiment, an access instrument includes an extension having a rim, the rim defining a first opening aligned with a central axis defined by the extension, and a second opening circumferentially opposite the first opening, and a body having a body length, a first slot having a first slot length from the rim and aligned with the first opening, and a second slot having a second slot length from the rim and aligned with the second opening, the first slot length and the second slot length being less than the body length. Further, the first slot length may be less than the second slot length.

BRIEF DESCRIPTION OF THE DRAWINGS

These and other features, aspects, and advantages of the present invention will become better understood with regard to the following description, and accompanying drawings where:

FIG. 2A depicts a perspective view of an access instrument according to another embodiment of the invention.

FIG. 2B depicts a side view of the access instrument of FIG. 2A.

DETAILED DESCRIPTION

As used herein, the words "proximal" and "distal," when used in connection with a medical device, refer to a position closer to and farther away from, respectively, a surgeon using the medical device. Thus, for example, the end of the medical device farthest from a surgeon would be the distal end of the medical device, while the end opposite the distal end and closest to a surgeon of the medical device, would be the proximal end of the medical device.

Although the present invention is largely discussed in connection with spinal MIS, the devices and methods disclosed herein have applicability to other types of surgeries. Nonetheless, for purposes of describing the present invention, it will be discussed in the context of a spinal discectomy, which may be performed in a minimally invasive manner by cutting a small incision in the tissue near the disc and pushing an access instrument into the incision down to the spine in order to provide a working portal for the surgery. Other instruments, such as burrs, are thereafter inserted within the port to perform other aspects of the surgery.

During such a spinal discectomy procedure, the inserted instruments may be required to move around an area in the tissue proximal to the vertebral disc, called Kambin's triangle. In this manner, the access instrument cannot penetrate directly to the vertebral disc and requires the inserted tools to move aside the muscles and nerves within Kambin's triangle. For example, burrs must go around the muscles and nerves in a scoop-like fashion such that the burrs can remove the spinal disc while minimizing potential damage to the surrounding tissue. This scooping movement requires a degree of angular access to both the contralateral and ipsilateral side of the incision. Additionally, visibility issues may arise where more than one instrument is inserted as the confined space can quickly render the use of one instrument blocking the view of the other. These problems are exacerbated as the access instrument increases in length, further reducing the visibility and angular movement of the inserted instruments as they are further distally inserted within the working portal.

Figures 1A, 1B:
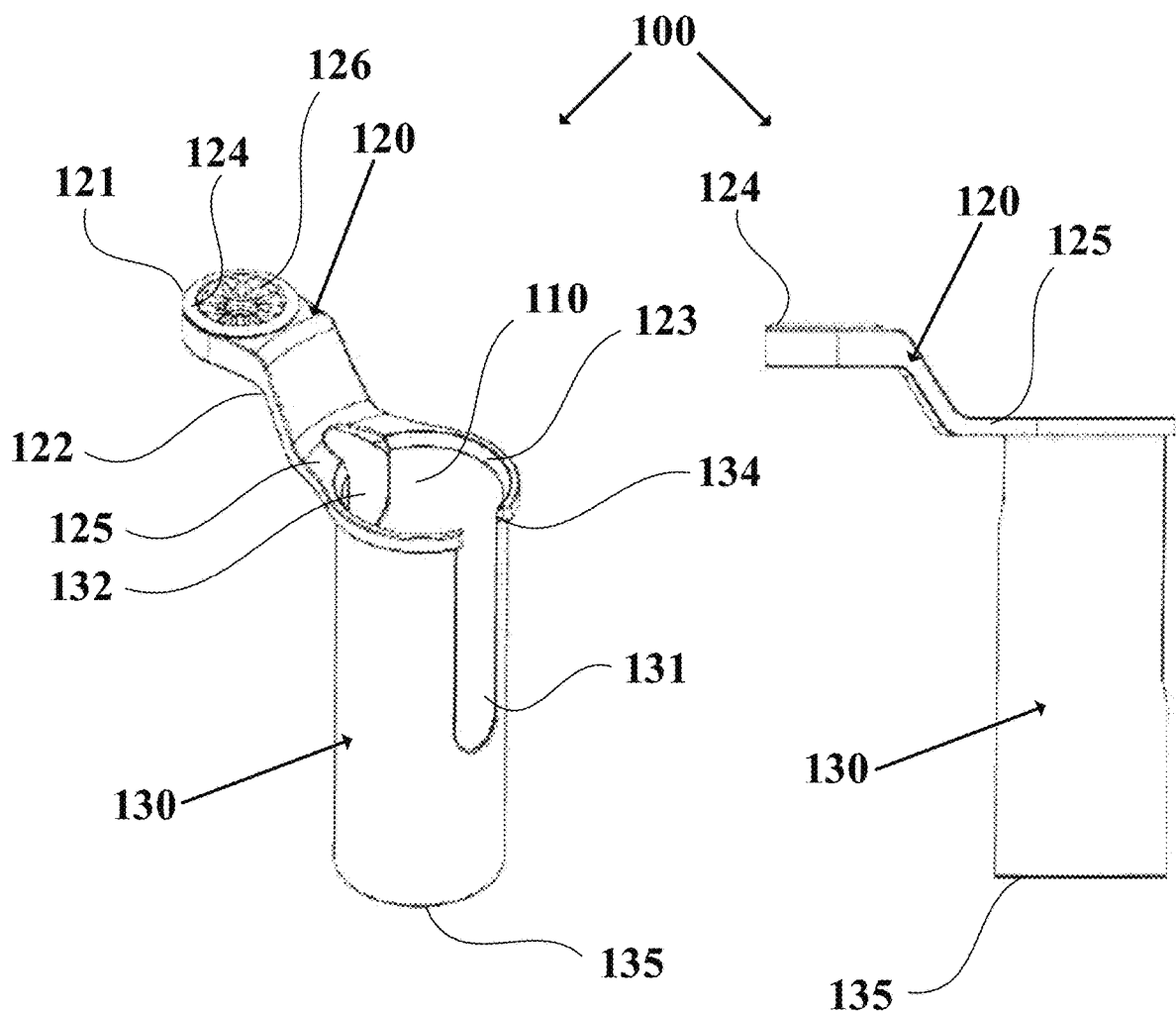
FIG. 1A depicts a perspective view of an access instrument according to one embodiment of the invention.
FIG. 1B depicts a side view of the access instrument of FIG. 1A.

The present disclosure describes an access instrument that allows for a greater range of angular motion and visibility for surgical instruments inserted within a working portal created by the access instrument. FIGS. 1A-1B depict an access instrument 100 having an extension (or top portion) 120 and a body (or tube) 130. FIG. 1A depicts a perspective view of access instrument 100 and FIG. 1B depicts a side view of access instrument 10. Extension 120 has an engagement portion (or first portion) 121, intermediate (or second portion) 122, and rim (or third portion) 123. Engagement portion 121 has an exterior surface at an end of engagement portion 121 having a partially-cylindrical shape and substantially planar surfaces extending toward intermediate portion 122. Engagement portion 121 has a larger thickness than intermediate portion 122 and rim 123 to provide a more secure connection when engaged with a mounting arm. Engagement portion 121 has a hirth joint (or securement portion) 126, surrounded by brim 124, that is recessed within engagement portion 121 and concentric with brim 124. Brim 124 extends from engagement portion 121 a distance to assist in preventing debris from entering hirth joint 126 as engagement portion 121 is secured to a mounting arm (not shown). Hirth joint 126 is allows for a mounting arm to connect to access instrument 10 at a variety of angles. Intermediate portion 122 proximally extends from transition (or fourth) portion 125 of rim 123, described below, to engagement portion 121 at an off-set angle. Transition portion 125 increases in width from intermediate portion 122 to smoothly transition to the circumference of rim 123. The corners between engagement portion 121 and intermediate portion 122, and intermediate portion 122 and rim 123 are rounded on both the distal and proximal surfaces to allow for a smooth transition between the respective portions of extension 120. Intermediate portion 122 has a substantially flat outer surface and gradually increases in width from the end connected to engagement portion 121 to the end connected to transition portion 125. Rim 123 defines opposing openings respectively aligned with slots 131, 132 of body 130, as described further below, that aid in serving as relief areas an instrument to temporarily pass through. The opening aligned with slot 132 is substantially oval-shaped and extends partially through the central region of transition portion 125. The opening aligned with slot 131 and opposite to the opening aligned with slot 132 is defined between two ends of rim 123. Rim 123 circumferentially extends a distance from body 130 to provide a lip that prevents access instrument 10 from being inserted too far within the working portal of the patient. In this manner, access instrument 10 can be distally inserted a distance up to a distal surface of rim 123. The corners of inner circumference of rim 123 has a chamfered edge to allow for instruments to more easily slide along rim 123 during insertion into the working portal.

Figure 3:
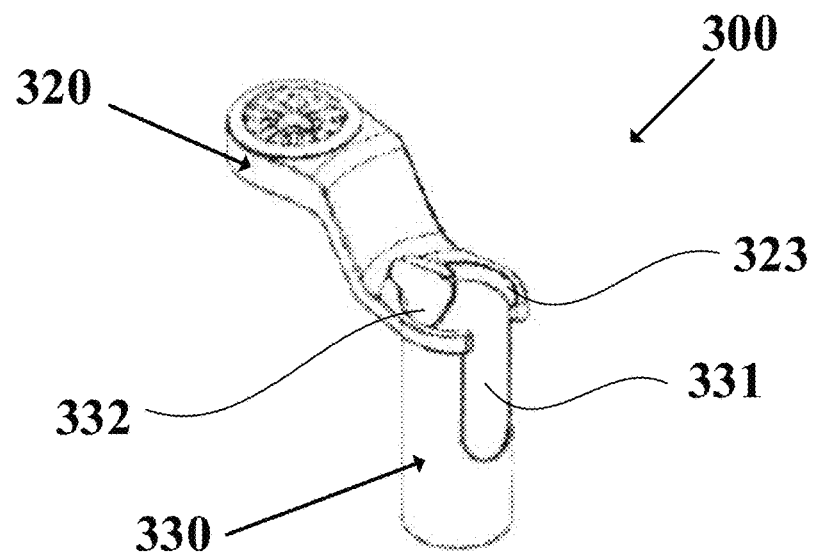
FIG. 3 depicts a perspective view of an access instrument according to another embodiment of the invention.

In an alternative embodiment, it is envisioned that the angle between engagement portion 121 and intermediate portion 122, and rim 123 and intermediate portion can be either equal, as shown, or different (e.g., 30 degrees between intermediate portion 122 and engagement portion 121, 45 degrees between intermediate portion 122 and rim 123). In yet another embodiment, it is envisioned that there are no such angles and engagement portion 121 is level with rim 123. In yet other embodiments, it is envisioned that engagement portion 121 has substantially the same thickness as intermediate portion 122 and rim 123. Although hirth joint 126 is depicted for use in securing engagement portion 121, other securement means may be used instead (e.g., threads, clamps, or the like). The corners between engagement portion 121/rim 123 and intermediate portion 122 may additionally have alternative shapes other than being rounded (e.g., chamfered, sharp-cornered, or the like). In other embodiments, it is envisioned that the surface of intermediate portion 122 is not flat and may be, for instance, curved to provide increased structural strength. In yet other embodiments, it is envisioned that extension 120 has a substantially uniform width throughout, as shown in FIG. 3, described below. The opening aligned with slot 132 may have alternative shape other than being an oval (e.g., square, triangular, or the like). In a further alternative embodiment, rim 123 only includes one opening. Additionally, the openings respectively aligned with slots 131, 132 may have differing widths. In other embodiments, rim 123 does not have an inner chamfered edge and may have alternative edges (e.g., a sharp corner, rounded edge, or the like).

Body 130 is a substantially cylindrical tube having a first end 134 and second end 135 with a central passageway 110 running therethrough. First end 134 is a substantially circular edge encompassed by rim 123 while second end 135 is a substantially circular edge opposite the first end. Second end 135 defines a circumferential plane parallel to a circumferential plane at first end 134. Body 130 has a first slot 131 opposite second slot 132, each of the slots having a substantially equal width but differing lengths. However, alternative embodiments may have slots 131, 132 circumferentially lie along any portion of body 130 (e.g., at a perpendicular angle from each other). First slot 131 and second slot 132 has a substantially uniform width running along their lengths from the proximal end to a circular distal end however second slot 132 has a shorter length than first slot 131. As mentioned above, slots 131, 132, and their respectively aligned openings on rim 123, are circumferentially opposite each other. In a preferred embodiment, slot 132 is aligned beneath extension 120 while slot 131 sits on the opposite side to reduce the number of access instruments that may be required during surgery from slots having alternative orientations. For instance, where the slots are aligned in a first access instrument such one slot is at 90 degrees from the other, a second access instrument may be required having an alternative orientation in order for the surgeon to gain appropriate access to the working site within the patient.

In a preferred embodiment, first slot 131 travels down 60% of the length of body 130 from first end 134 while second slot 132 travels down 20% of the length of body 130 from first end 135. In this manner, multiple instruments may be inserted within the central passageway 110 of body 130 such that one instrument may contralaterally pass through first slot 131 while a second instrument may ipsilaterally pass through second slot 132. This allows for one instrument to, for example, push back the nerves and tissue in front of a vertebral disc, and create access and visibility for another instrument to access the vertebral disc itself. Alternatively, there might only be one instrument that passes through either of first slot 131 and second slot 132 first before passing through the other.

In other embodiments, either or both of the distal ends of first slot 131 and second slot 132 has a non-circular shape (e.g., square, triangular, or the like). Additionally, either or both of the widths of first slot 131 and second slot 132 may be non-uniform (e.g., taper from a wider proximal end to a narrower distal end or vice versa, having a first section of the slot with a different width than a second section of the slot, or the like). In other embodiments, the widths of first slot 131 and second slot 132 are different, such that the width of either the first slot 131 or second slot 132 is greater than the other. In yet other embodiments, it is envisioned that second slot 132 is longer than first slot 131, or second slot 132 has an equal length to first slot 131. Alternatively, either or both of first slot 131 and second slot 132 may run the full length of body 130. In yet other aspects, first slot 131 and second slot 132 may go down any percentage of the length of body 130 (e.g., 70% for first slot 131 and 30% for second slot 132, 50% for first slot 131 and 10% for second slot 132, or the like). Body 130 may alternatively have a non-tubular (e.g., rectangular, triangular, or the like). In yet other embodiments, it is envisioned that either/both of first slot 131 and second slot 132 run along the length of body 130 from second end 135 rather than first end 134. Further, there may be more or less than two slots 131, 132.

Figure 5:
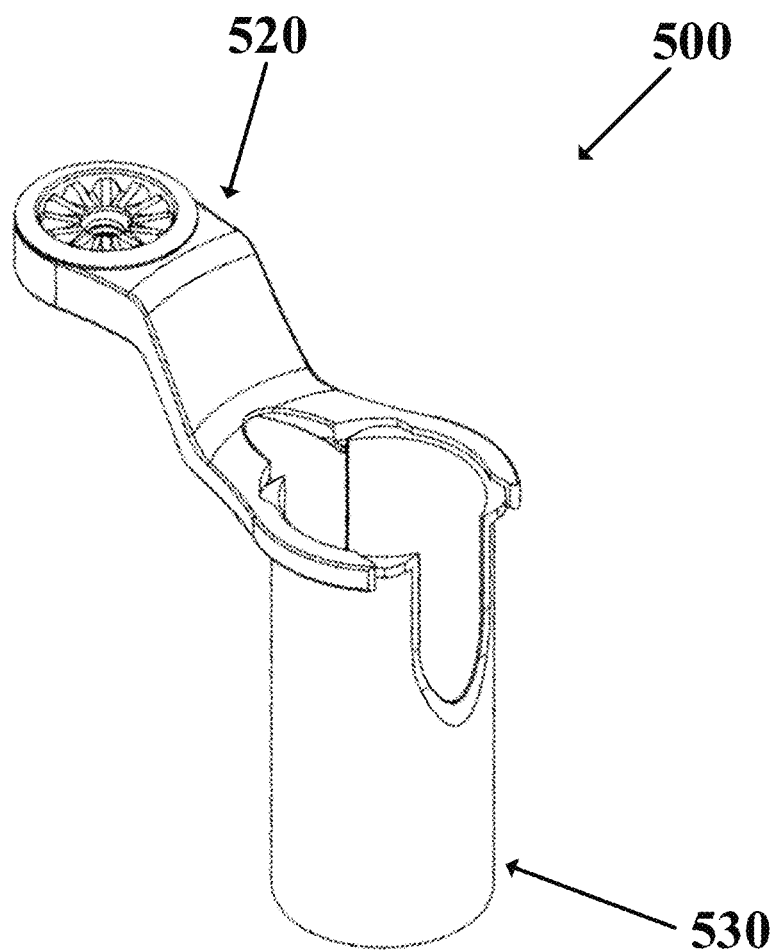
FIG. 5 depicts a perspective view of an access instrument according to another embodiment of the invention.
Figure 6:
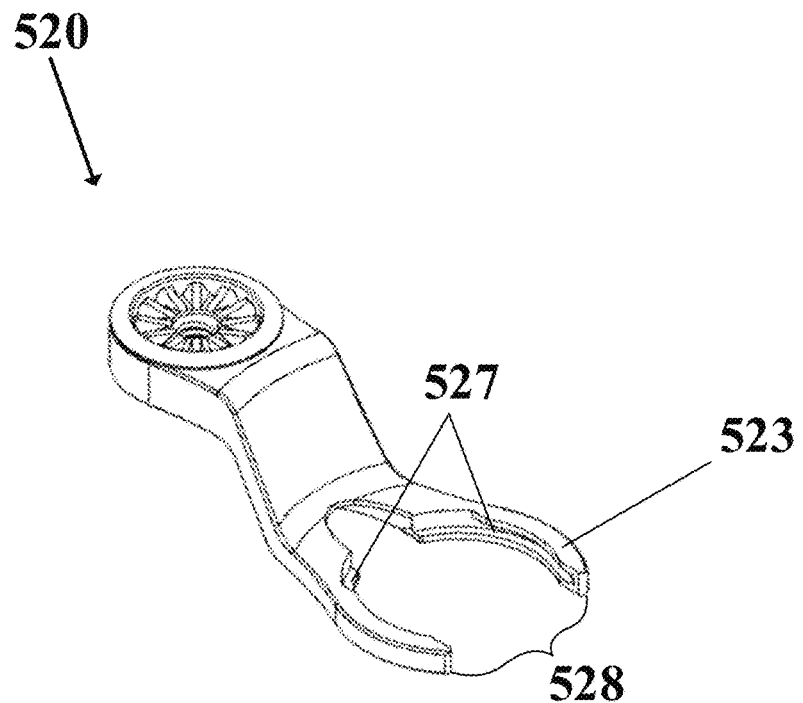
FIG. 6 depicts a perspective view of an extension of the access instrument of FIG. 5.
Figure 7:
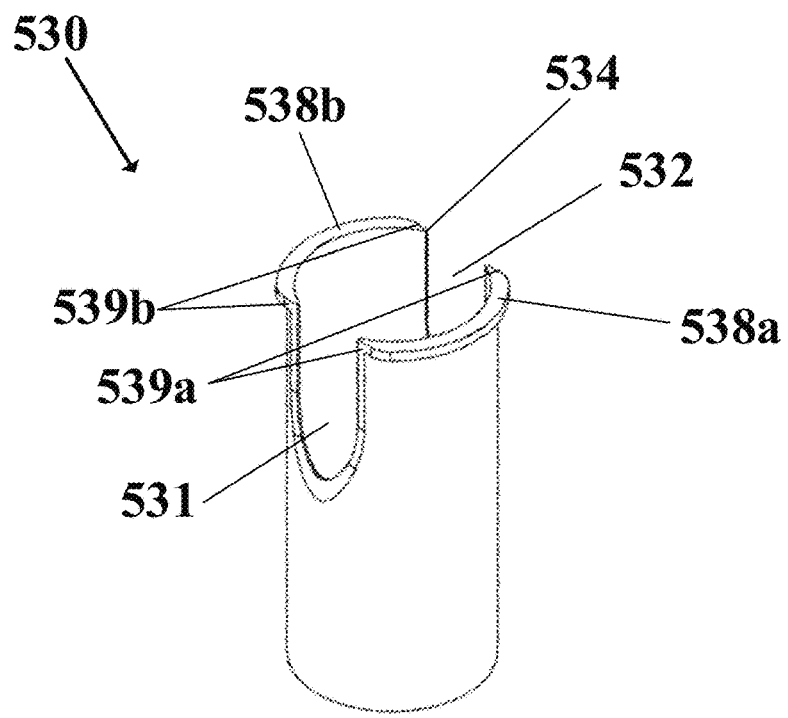
FIG. 7 depicts a perspective view of a body of the access instrument of FIG. 5.

In a preferred embodiment, access instrument 100 may be monolithically constructed such that extension 120 and body portion 130 are integral with each other. Alternatively, extension 120 and body portion 130 may be separately constructed before being connected (e.g., by being glued together, press-fit, or the like), as shown in FIGS. 5-7, below. In this manner different sized or shaped extensions and bodies can be combined together as desired by the surgeon (e.g., the extension 120 having a length corresponding to the length of second slot 132). However, having access instrument 10 constructed of one solid piece may allow for increased structural stability.

Access instrument 100 is preferably constructed of a rigid material, such as stainless steel, or the like. However, in an alternative embodiment, it is envisioned that body 130 may be constructed of a flexible material, such as silicone, spring steels, or the like. In this manner, first slot 131 and second slot 132 may be partially deformed to temporarily increase the amount of angulation available to the instruments passed through those slots during use.

It is envisioned that, in other embodiments, the circumferential plane of second end 135 is not parallel to the circumferential plane of first end 134. FIGS. 2A-2B depicting another example access instrument 200 having an extension 220 and body 230, as described above. In this embodiment, second end 235 has a circular edge that defines a first circumferential plane at an angle to a second circumferential plane defined at first end 234. Second end 235 has a leading (or first) point 236 and a trailing (or second) edge 237. In this manner, access instrument 200 may be more easily inserted within an incision of the patient as the incision can be gradually expanded from a small contact area defined by leading point 236 to the entire circumference of body 230 once trailing edge 237 enters the patient. This minimized initial contact area may additionally assist in inserting access instrument 200 at an angle that is not perpendicular to the patient. Other features of access instrument 200 are similar to those of access instrument 100 and like reference numerals are utilized, but within the 200-series of numbers.

FIG. 3 depicts a perspective view of access instrument 300 having extension 320 and body 330, as described above. In this embodiment, extension 320 has a uniform width along its length. Body 330 is shorter and has a smaller circumference relative to extension 320 than body 130 relative to extension 120 of access instrument 100, as shown in FIGS. 1A-1B. Additionally, first slot 331 and second slot 332, along with their corresponding openings along rim 323, have a larger relative width than the corresponding features of access instrument 100. Otherwise, other features of access instrument 300 are similar to those of access instrument 100, 200 and like reference numerals are utilized, but within the 300-series of numbers.

Figure 4:
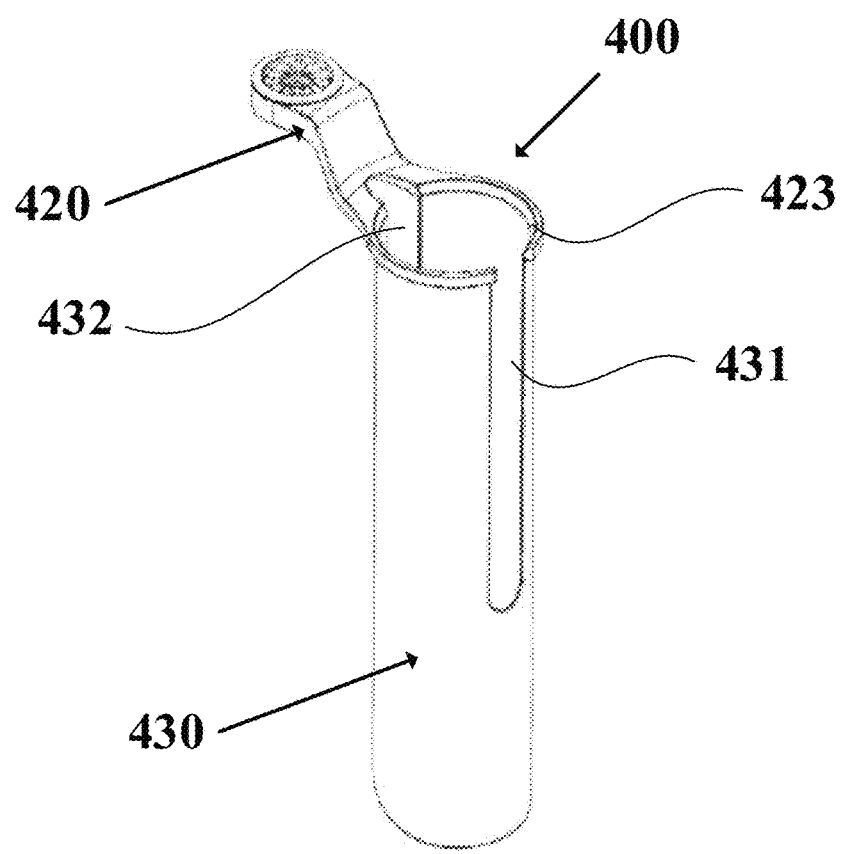
FIG. 4 depicts a perspective view of an access instrument according to another embodiment of the invention.

FIG. 4 depicts a perspective view of access instrument 400 having extension 420 and body 430, as described above. In this embodiment, body 430 is longer and has a larger circumference relative to extension 420 than body 130 relative to extension 120 of access instrument 100, as shown in FIGS. 1A-B. Additionally, first slot 431, and second slot 432, along with their corresponding openings along rim 323, have a smaller relative width than the corresponding features of access instrument 100. Otherwise, other features of access instrument 400 are similar to those of access instrument 100, 200, 300 and like reference numerals are utilized, but within the 400-series of numbers.

FIGS. 5-7 depict a perspective view of another embodiment access instrument 500 having an extension 520 and body 530. In this embodiment, extension 520 and body 530 are separately constructed from each other. When extension 520 and body 530 are engaged, the body can swivel relative to the extension about a longitudinal axis defined by the body. FIG. 6 depicts extension 520 similar to those described above, except rim 523 defines a channel 527 running along the circumference of the rim. Rim 523 defines a gap 528 between two ends of the rim. FIG. 7 depicts body 530 similar to those described above, except body 530 includes lips 538a,b radially protruding from the body at first end 534. Other features of access instrument 500 are similar to those of access instrument 100, 200, 300, 400 and like reference numerals are utilized, but within the 500-series of numbers Lips 538a,b can protrude a distance sized to be received within channel 527 of rim 523 such that body 530 can swivel relative to extension 520 while remaining axially fixed. Lips 538a,b respectively include substantially planar end portions 539a,b. End portions 539a,b are respectively aligned with each side of slots 531, 532. End portions 539a defines a first linear distance between each other and end portions 539b defines a second linear distance between each other. The first and second linear distances are substantially equal, and match the distance of gap 528. In this manner, body 530 can be slid within gap 528 through end portions 539a,b being received within gap 528 until body 530 is concentrically aligned with rim 523. Body 530 can then be swiveled relative to extension 520 such that channel 527 receives lips 538a,b.

Figure 8:
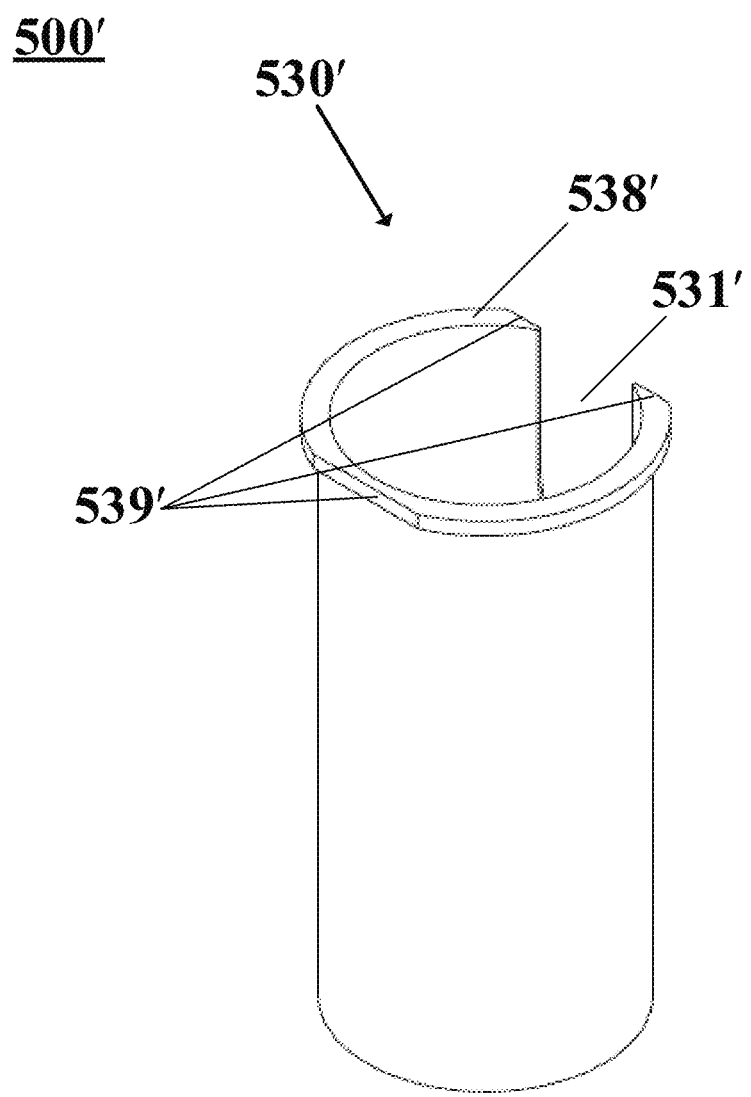
FIG. 8 depicts a perspective view of a body of an access instrument according to another embodiment of the invention

In alternative embodiments, the first and second linear distances respectively defined by end portions 539a,b can be different from each other. In a further alternative embodiment, one or both of first and second linear distances is less than the distance of gap 528. In a yet further embodiments, body 530 can have more or less than two slots 531, 532. For instance, FIG. 8 depicts access instrument 500' body 530' having one slot 531' with one lip 538' and end portions 539'. Alternatively, access instrument 500 can have more than two slots 531, 532. In this example, each slot can have a different length so that a surgeon can select a desired slot length by rotating body 530 relative to extension 520 to align one or more of the desired slots with one or more of the opening defined by rim 523. Further, access instrument 500 can be presented to the surgeon with both extension 520 and body 530 already engaged with each other however, in alternative embodiments, a number of extensions and bodies can be presented to the surgeon in a kit. In this manner, the surgeon can select from any number of bodies 530 having different configurations of slots, lengths, or the like to engage with extension 520.

Figures 9A, 9B:
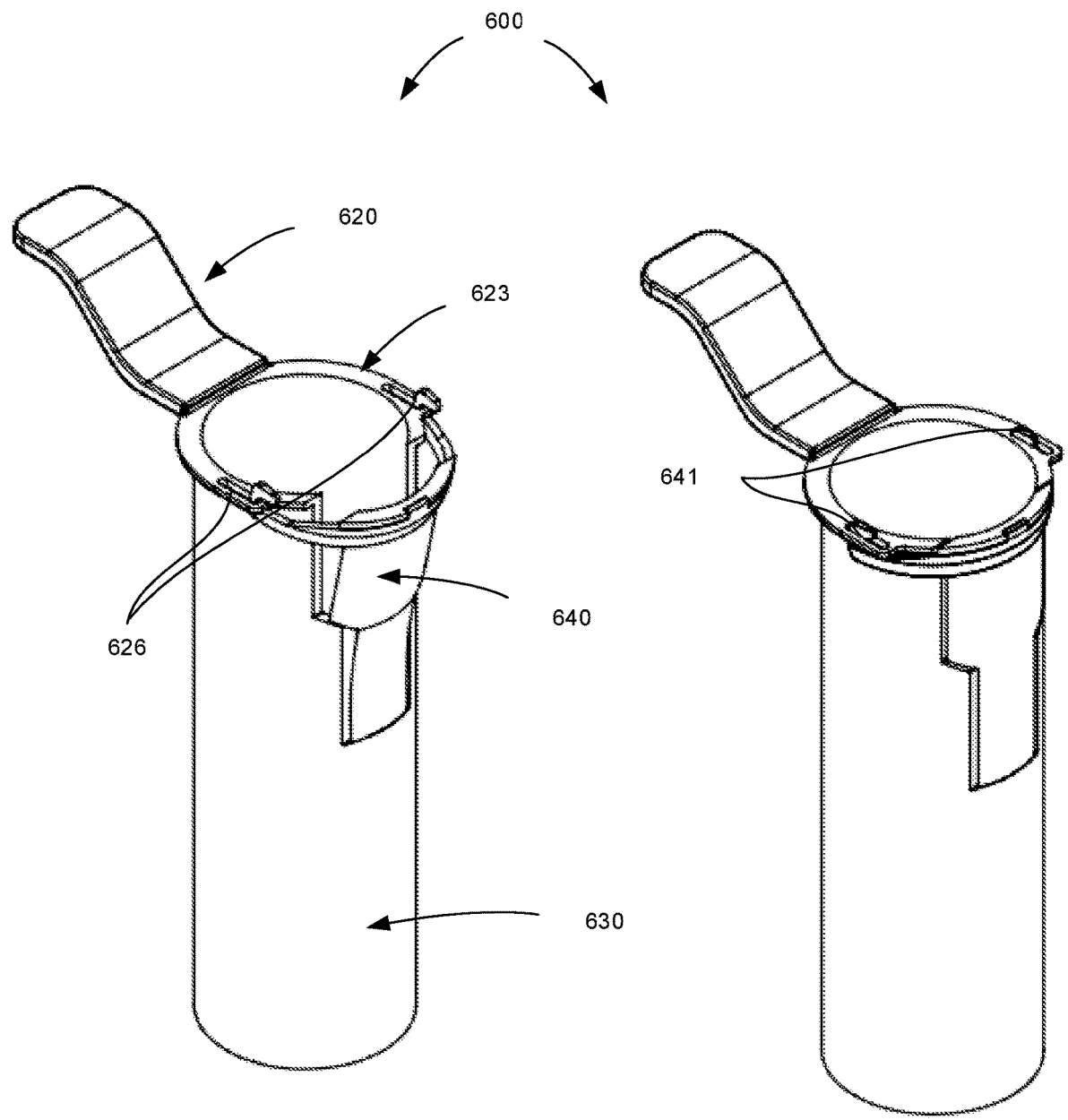
FIG. 9A depicts a perspective view of an access instrument according to another embodiment of the invention.
FIG. 9B depicts a perspective view of the access instrument of FIG. 9A after the elastic portion has been manipulated.

FIGS. 9A-B depicts a perspective view of another example access instrument 600. In this embodiment, body 630 has an elastic portion 640 running along a length of body 630 from rim 623. Elastic portion 640 has hooks 641 such that, when elastic portion 640 is manipulated by the surgeon, hooks 641 engage with openings 626 of rim 623 to create a slot extending from rim 623 defined between rim 623 and the proximal region of elastic portion 640, as shown in FIG. 9B. Elastic portion 640 has a staggered width such that a first proximal portion has a greater width than a second distal portion, with a linear taper connecting the first proximal portion and the second distal portion. In other embodiments, elastic portion 640 may have a substantially uniform width. Alternatively, elastic portion 640 may have a linear taper from a wider proximal end to a thinner distal end along either the entire length or a portion of the length thereof. Other features of access instrument 600 are similar to those of access instrument 100 and like reference numerals are utilized, but within the 600-series of numbers.

Figure 10:
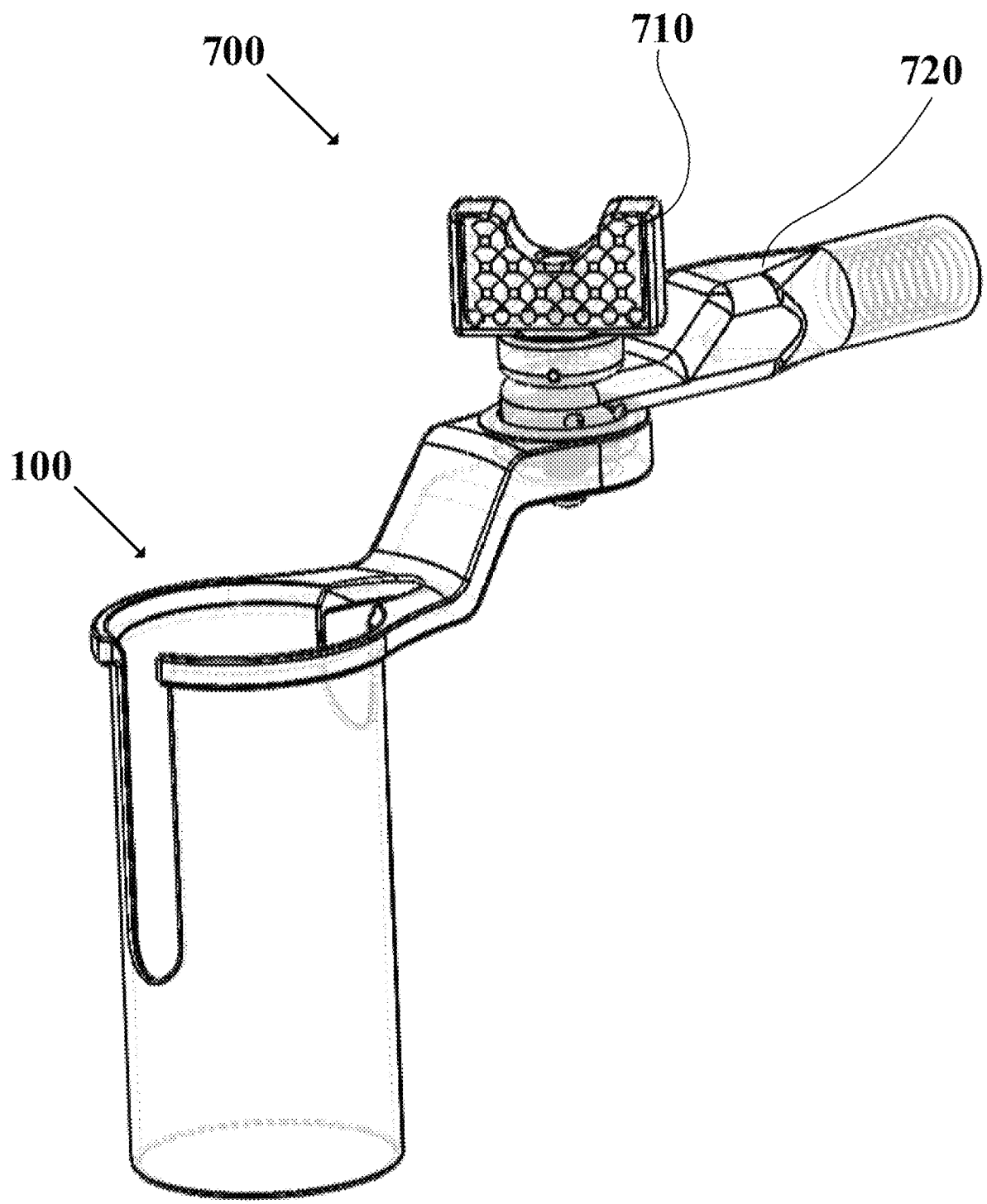
FIG. 10 depicts a perspective view of the access instrument of FIGS. 1A-B in use with a table mounting arm according to another embodiment of the invention.

Access instrument 100 may come in a set with accessories. For instance, FIG. 10 depicts a mounting arm 700 connected to access instrument 100 through extension 120 and hirth joint (not shown). Mounting arm 700 has a knob 710 and connecting arm 720. Knob 710 may be rotated in a first direction to secure access instrument 100 and in a second direction release access instrument 100. Connecting arm 720 extends from knob 710 to allow for greater stability and control over access instrument 100 when mounting arm 700 is connected to access instrument 100.

Figure 11:
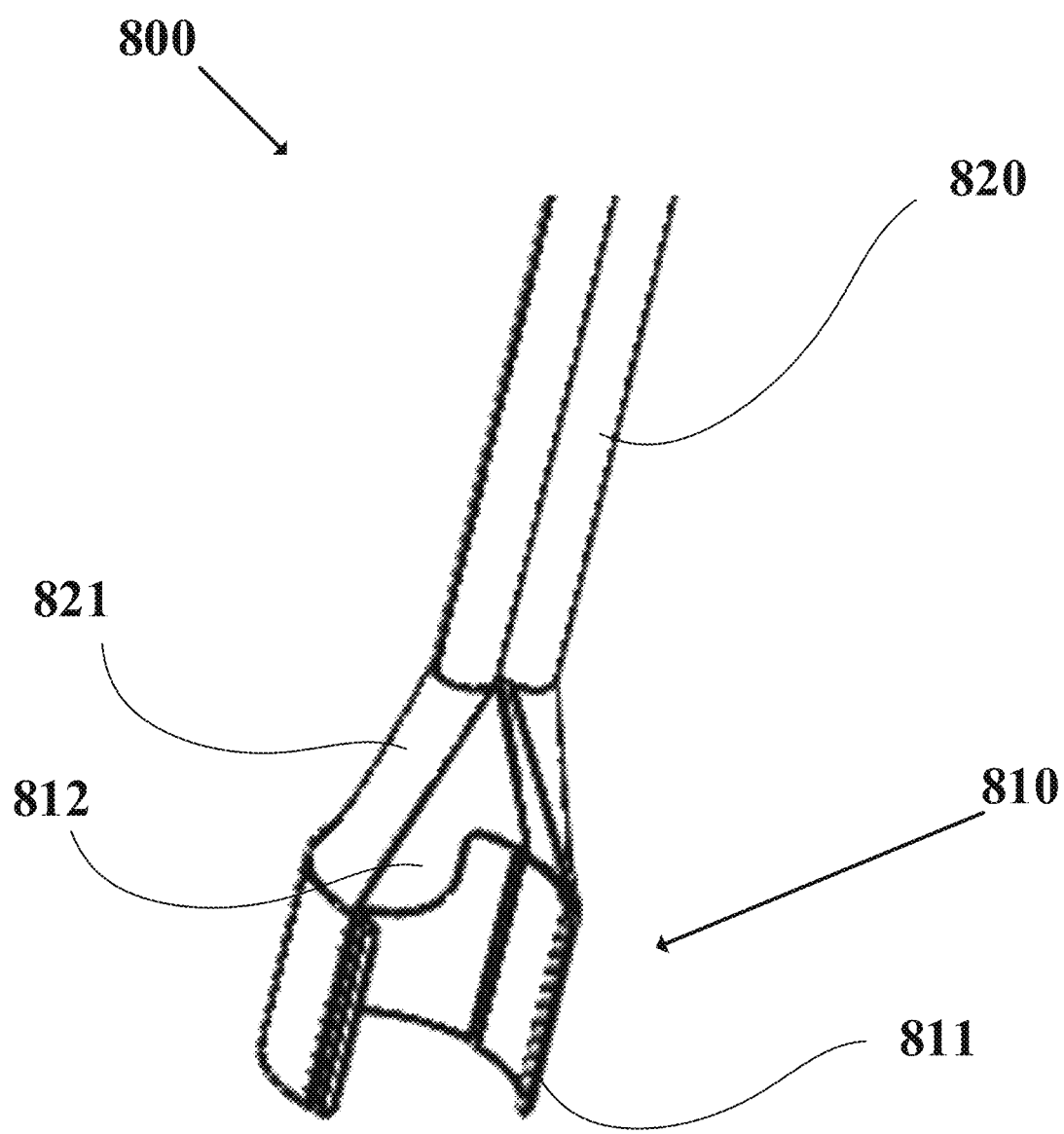
FIG. 11 depicts a perspective view of a lighting device according to another embodiment of the invention.

FIG. 11 depicts a lighting device 800 having a head 810 and arm 820. Arm 820 has two rigid tubular portions that splits off at a distal end to create divergent legs 821. A proximal portion of head 810 is connected to a distal end of legs 821. Head 810 is shaped to fit within access instrument 100, as shown in FIGS. 1A-B, such that an exterior surface of head 810 is in contact and flush with an interior surface of central passageway 110. Head 810 includes a slot 812, defined along a length of head 810, in communication with the space created between legs 821 to allow for an instrument to be inserted therethrough. Head 810 further includes light sources 811 opposite slot 812 and is aligned along the edges of head 810. Light sources may be in the form of a variety of light sources, such as light-emitting diodes, fluorescent bulbs, incandescent bulbs, or other forms of light-emitting sources.

Figure 12A:
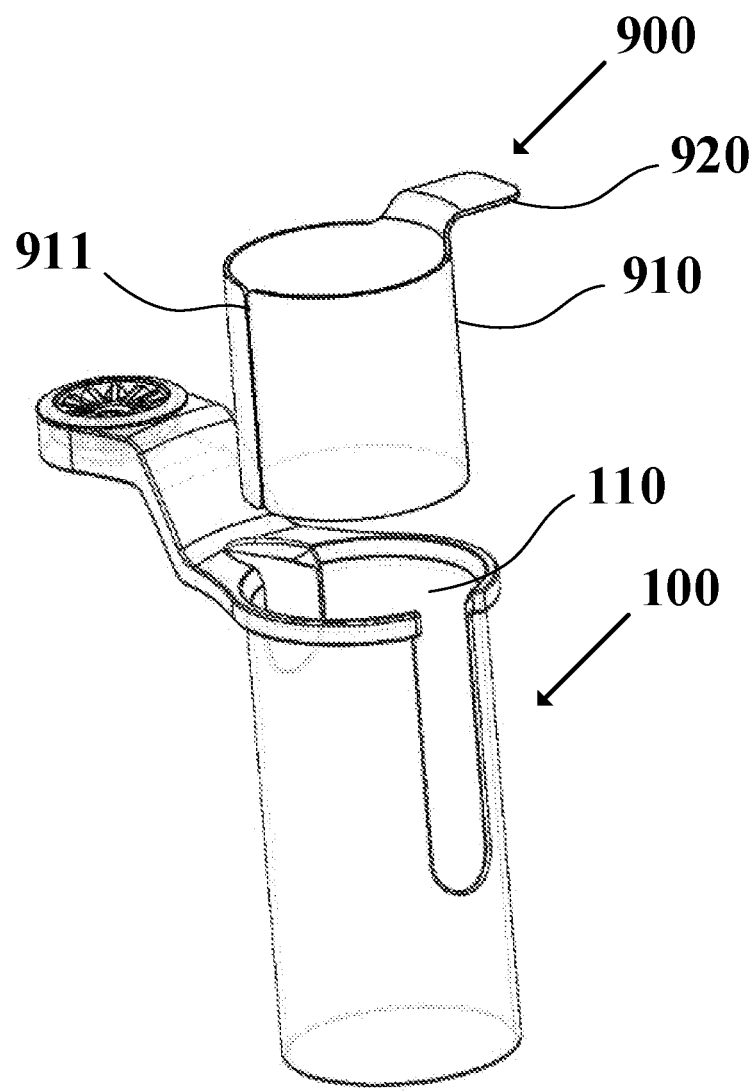
FIG. 12A depicts a perspective view of the access instrument of FIGS. 1A-B in use with a shim according to one embodiment of the invention.
Figure 12B:
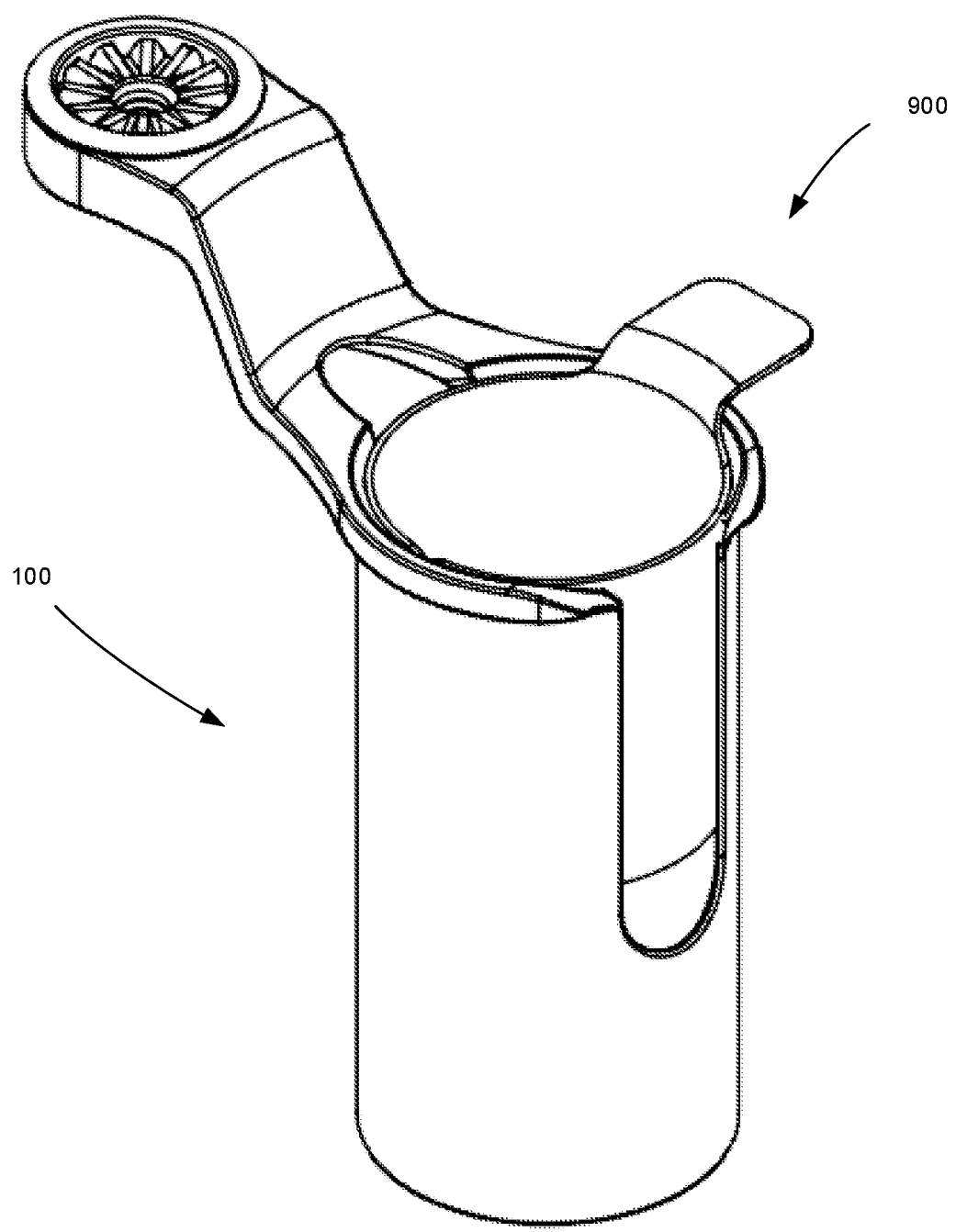
FIG. 12B depicts a perspective view of the access instrument and shim of FIG. 8A after the shim has been inserted into the access instrument.

FIGS. 12A-B depicts a shim 900 inserted within central passageway 110 of access instrument 100. FIG. 12A depicts shim 900 prior to being inserted within access instrument 100 while FIG. 912B depicts shim 900 after being inserted within access instrument 100. Shim 900 has a body 910 and tab 920. Body 910 is substantially cylindrical with an opening running therethrough and includes two edges opposite tab 920 defining a slit 911 running along the length of body 910. Body 910 provides structural support to access instrument 100 to prevent or minimize any tissue creep. Tab 920 extends from body 910 to allow for a surgeon to grasp and maneuver during surgery.

Access instrument 100 may also have a chemically neutral coating around an exterior surface to allow for easier insertion, minimizing any potential negative chemical reactions with the patient, and reducing glare from light reflected off the access instrument.

Figure 13:
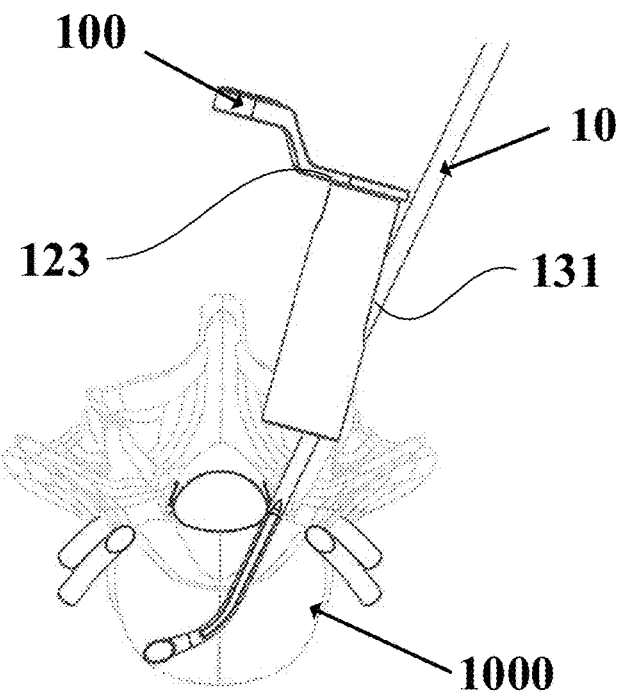
FIGS. 13-15 depict methods of using the access instrument of FIGS. 1A-B.
Figure 14:
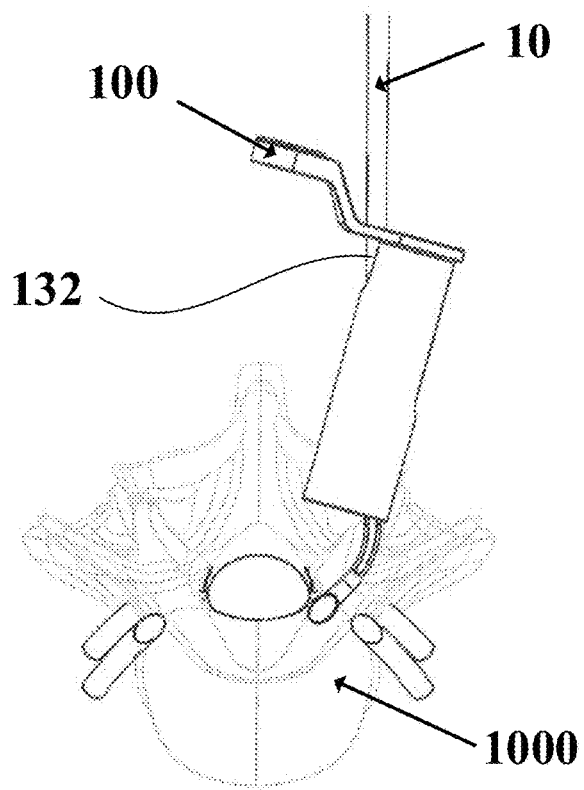

An exemplary method of use will now be discussed with reference to FIGS. 13-14, which depict access instrument 100 inserted within the body to a position adjacent the spine. An instrument 10 is then inserted within the central passageway 110. FIG. 13 depicts access instrument 10 contralaterally maneuvered through first slot 131 and the corresponding opening along rim 123, while FIG. 14 depicts access instrument 10 ipsilaterally maneuvered through second slot 132 and the corresponding opening along rim 123. The differing length of slots 131 can result in instrument 10 having a different maximal angle relative to access instrument 100, depending on which slot is used. For instance, the maximum relative angle between instrument 10 and body 130 through first slot 131 can be greater than the corresponding angle when instrument 10 is maneuvered through second slot 132. In this manner, instrument 10 can maneuver around certain tissue (not shown) surrounding a vertebral body 1000, such as within Kambin's triangle. Note that instrument 10 can be maneuvered through either first slot 131 or second slot 132 in any order, or only through one of the slots, as desired by the surgeon.

Figure 15:
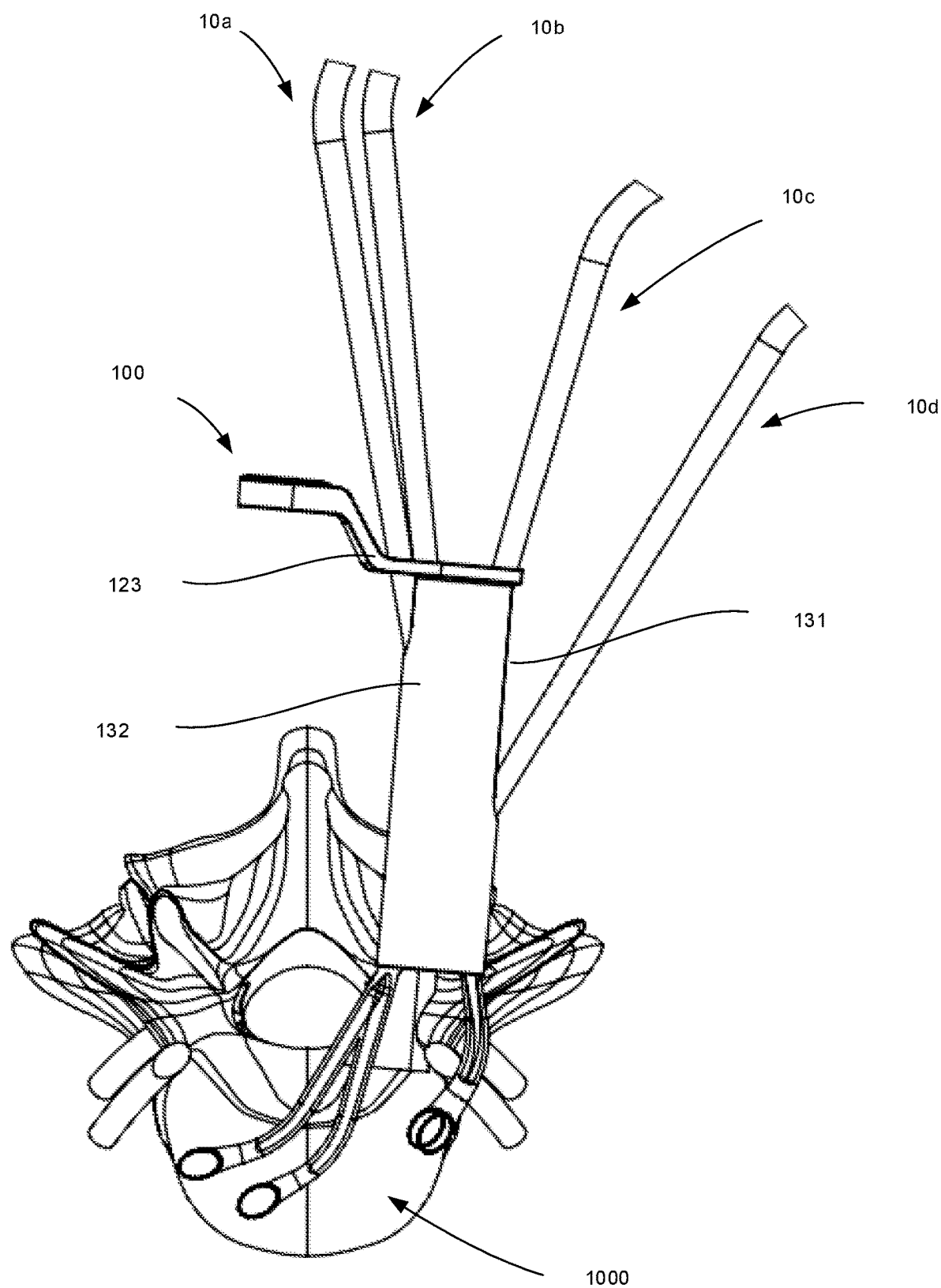

In another method of use, FIG. 15 again depicts access instrument 100 having been inserted within an incision (not shown) to create a working portal. In this embodiment, multiple instruments 10a, 10b, 10c, 10d are inserted within access instrument 100 after access instrument 100 has been inserted within the patient. Instrument 10a is inserted within the working portal and then ipsilaterally maneuvered through second slot 132 and the corresponding opening along rim 123 to push aside tissue (not shown) surrounding vertebral body 1000. Then access instrument 100 is inserted within access instrument 100 and contralaterally maneuvered through first slot 131 and the corresponding opening along rim 123 to access the spinal disc (not shown) of vertebral body 1000. As first slot 131 is longer than second slot 132, maneuvering instrument 10d can result in a greater angle between instrument 10d and access instrument 100 compared to the angle between instrument 10a and access instrument 100. Note that not all of instruments 10a, 10b, 10c, 10d inserted within access instrument 100 are required to pass through the slots. For example, instrument 10d is maneuvered through first slot 131 but instrument 10c is not. Similarly, instrument 10a is maneuvered through second slot 132 but instrument 10b is not. In an alternative embodiment, it is envisioned that any number of instruments can be used as desired by the surgeon (e.g., two instruments, three instruments, or the like). Instruments 10a, 10b, 10c, 10d may be inserted and removed in any order desired by the surgeon. Additionally, intermediate steps in the surgery may be performed between the insertion/removal of instruments 10a, 10b, 10c, 10d.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An access instrument for creating a surgical working portal, comprising:
   a body having an upper portion, a lower monolithic portion, a first end, and a body length;
   an extension extending from a transition portion of the upper portion of the body;
   a first slot defined by a rim and having a first slot length running along the length of the body from the first end; and
   a second slot defined by the transition portion and having a second slot length running along the length of the body from the first end and in line with the extension, wherein the first slot length and the second slot length are less than the body length and the first and second slots extend entirely through the body.

2. The access instrument of claim 1, wherein either of the first slot length and the second slot length is greater than the other.

3. The access instrument of claim 1, wherein the first slot length and the second slot length are equal.

4. The access instrument of claim 1, wherein the first slot has a first width and the second slot has a second width, either of the first slot and the second slot being greater than the other.

5. The access instrument of claim 1, wherein the extension g has an engagement portion, the rim attached to the first end of the body, and an intermediate portion between the engagement portion and the rim.

6. The access instrument of claim 5, wherein a first angle is formed between the intermediate portion and the engagement portion, and a second angle is formed between the intermediate portion and the rim, and the intermediate portion extends a proximal distance from the rim.

7. The access instrument of claim 5, wherein the extension is rotatable with respect to the body.

8. The access instrument of claim 5, the rim defining a first circumferential plane and the body having a second end longitudinally opposite the first end defining a second circumferential plane, the first circumferential plane being either parallel or at a planar angle from the second circumferential plane.

9. The access instrument of claim 5, wherein the intermediate portion extends from a transition portion of the rim, the transition portion defined between the intermediate portion and the rim.

10. The access instrument of claim 9, wherein the rim defines a first opening along a portion thereof and the transition portion defines a second opening along a central region of the transition portion.

11. The access instrument of claim 10, wherein the first slot of the body is aligned with the first opening and the second slot is aligned with the second opening.

12. The access instrument of claim 10, wherein the first opening and the second opening are circumferentially opposite each other.

13. The access instrument of claim 10, wherein the first opening has a first distance and the second opening has a second distance, either of the first distance and the second distance being greater than the other.

14. A method of using an access instrument, comprising:
inserting a first instrument within a passageway running through a port, and a body having a body length, an upper portion, a lower monolithic portion, and a first end;
inserting a second instrument within the passageway;
maneuvering the first instrument through a first slot defined by a rim and formed entirely through the body and having a first slot length running along the length of the body from the first end; and
maneuvering the second instrument through a second slot defined by a transition portion and formed entirely through the body and having a second slot length running along the length of the body from the first end, wherein each of the first slot length and the second slot length is less than the body length and the first and second slots being opposite each other, the transition portion extending from the upper portion.

15. The method of claim 14, wherein the body defines a longitudinal axis, and maneuvering the first instrument forms a first angle between the first instrument and the longitudinal axis, and maneuvering the second instrument forms a second angle between the second instrument and the longitudinal axis, the first angle being greater than the second angle.

16. The method of claim 14, further comprising mounting the access instrument by connecting an extension of the access instrument to a mounting arm.

17. The method of claim 16, wherein the mounting step includes securing a securement portion to the mounting arm.

18. The method of claim 15, wherein the extension includes a rim defining a first opening and a second opening circumferentially opposite each other, and maneuvering the first instrument includes maneuvering the first instrument through the first opening and maneuvering the second instrument includes maneuvering the second instrument through the second opening.

19. An access instrument comprising:
an extension having a rim, the rim defining a first opening aligned with a central axis defined by the extension, and a second opening circumferentially opposite the first opening;
a body having an upper portion, a lower monolithic portion, a body length, a first slot defined by the rim and having a first slot length from the rim and aligned with the first opening, and a second slot defined by a transition portion extending from the upper portion and having a second slot length from the rim and aligned with the second opening, the first slot length and the second slot length being less than the body length, the first and second slots extending entirely through the body.

20. The access instrument of claim 19, wherein the first slot length is less than the second slot length.

* * * * *